United States Patent [19]

Mourany et al.

[11] Patent Number: 4,846,681

[45] Date of Patent: Jul. 11, 1989

[54] ORTHODONTIC BRACKET

[76] Inventors: Haitham E. Mourany; Randa B. Mourany, both of 4425 Valley Forge Dr., Fairview Park, Ohio 44126

[21] Appl. No.: 165,031

[22] Filed: Mar. 7, 1988

[51] Int. Cl.⁴ ............................................. A61C 7/00
[52] U.S. Cl. ...................................................... 433/11
[58] Field of Search ................................. 433/8, 11, 18

[56] References Cited

U.S. PATENT DOCUMENTS

| | | | |
|---|---|---|---|
| 3,052,028 | 9/1962 | Wallshein | 433/11 |
| 3,128,553 | 4/1964 | Begg | 32/14 |
| 3,835,539 | 9/1974 | Wallshein | 32/14 A |
| 3,854,207 | 12/1974 | Wildman | 32/14 A |
| 3,871,096 | 3/1975 | Wallshein | 32/14 A |
| 3,959,880 | 6/1976 | Andrews | 32/14 A |
| 4,023,274 | 5/1977 | Wallshein | 32/14 A |
| 4,260,375 | 4/1981 | Wallshein | 433/11 |
| 4,492,573 | 3/1984 | Hanson | 433/11 |
| 4,547,153 | 12/1984 | Taylor | 432/11 |
| 4,551,094 | 1/1985 | Kesling | 433/8 |

Primary Examiner—Robert Peshock
Attorney, Agent, or Firm—Polster, Polster and Lucchesi

[57] ABSTRACT

An orthodontic bracket is disclosed having a body, with the body having a face adapted to be secured to a tooth and a slot in the body for receiving an orthodontic arch wire. The bracket has a platen for biasing or forcing the arch wire into the slot and for holding the wire in the slot.

4 Claims, 1 Drawing Sheet

ORTHODONTIC BRACKET

BACKGROUND OF THE INVENTION

This invention relates to an orthodontic bracket for receiving and gripping an orthodontic arch wire.

Generally, orthodontics is a field of dentistry in which the position of the teeth are physically moved relative to one another and relative to the maxilla and mandible, such that after treatment the teeth are in proper relation to one another and to the facial skeletal structure of the patient. Treatment begins by the orthodontist examining the patient's mouth, both visually and radiographically, so as to determine the existing positions of the teeth and the structure of the maxilla and mandible. The orthodontist then plans a course of treatment to selectively move certain of the teeth so that after a period of active orthodontic treatment, the teeth will be disposed in proper positional relationship relative to one another and relative to the patient's facial skeletal structure. A variety of appliances are available for tipping the teeth, rotating them about a longitudinal axis of the tooth, or moving the teeth in posterior, anterior, buccal, or lingual direction. In addition, teeth may be expanded, contracted, intruded, torqued, or derotated, as decided by the treating orthodontist.

It is conventional to use a so-called arch wire to interconnect various teeth of the patient's upper arch or lower arch so as to apply desired forces to selected of the teeth so as to properly position these selected teeth in different stages of treatment. Typically, the arch wire consists of a relatively stiff but flexible wire of a suitable stainless steel or the like material which is carried by tubes and/or brackets on either the outside (buccal) or the inside (lingual) sides of the teeth, with the tubes and/or the brackets being secured to pads which in turn are bonded to the faces of the teeth. Forces can be applied to the teeth by selectively fixing or securing the wires to the tubes or to the pads.

In certain prior art bracket systems, the archwires are secured to the brackets bonded to the teeth by means of ligature wires or elastomeric ties which are wrapped around the archwire and the bracket. However, the installation of such ligature wires is difficult and time consuming and may not grip the archwire as securely as desired.

An archwire is oftentimes fixed by brackets to a desired number of teeth in a patient's arch. If certain of these teeth are out of a desired alignment with respect to one or with respect to a final position, it is possible to apply an expansive or compressive force on one or more desired teeth by deflecting the wire from its desired path and by securing the delected arch wire to the desired teeth so as to expand (i.e., to move the teeth bucally or outwardly) or to contract (i.e., to move the teeth lingually). However, this not only requires that archwire to be securely fastened to the teeth to be moved, but also to adjacent teeth which serve to anchor the archwire.

Of course, after the teeth have moved an incremental amount, the force applied by the archwire relaxes and thus requires periodic adjustment. However, in practice, the above-described ligature wires and elastomeric ties used to secure the arch wires may not grip the archwire as securely as desired, and are difficult to remove and re-apply. Elastomeric ties tend to creep and thus loose their tension.

A variety of brackets and spring clips are known for securing the arch wire to the brackets and for applying forces in a desired direction to the bracket and then to the teeth. Reference may be made to such U.S. Pat. Nos. as 3,128,553, 3,854,207, 3,871,096, 3,959,880, 4,023,274, and 4,551,094, which disclose various brackets having arch wire retention clips. Reference may also be made to U.S. Pat. Nos. 3,959,880 and 4,547,153, which disclose various clamps, clips, and pads used in conjunction with arch wires. Still further, resilient retaining members are disclosed in U.S. Pat. Nos. 4,260,375 and 4,492,573.

However, none of these prior art patents have made use of a bracket of the structure herein described which retains and increases the effect of the arch wire and allows conversion from one wire slot system to another.

SUMMARY OF THE INVENTION

Among the several objects and features of the present invention may be noted the provision of an orthodontic bracket which readily engages an arch wire so as to apply a continuous force to the arch wire thereby to retain and maximize the effect of the arch wire on the teeth while applying a relatively constant level of orthodontic corrective force to the selected teeth to be moved;

The provision of such an orthodontic bracket in which th spring retentive and pushing forces of the bracket make the bracket self-ligating, thus eliminating the need for ligating pliers or other instruments and which enables the clinician to secure the archwire to the bracket almost instantaneously at any desired position along the wire;

The provision of such a bracket which permits control over uprighting and torquing forces which may be applied to a person's selected teeth thereby to correctively restore the teeth to their proper positional locations relative to one another and relative to the patient's jaws;

The provision of such an orthodontic bracket which can be utilized to effect uprighting of the tooth and control torque applied to the tooth;

The provision of such an orthodontic bracket which enables the ready insertion and removal of the arch wire and which readily accommodates different sizes and shapes of arch wires;

The provision of such a bracket which may be readily fabricated of metal or of a cosmetic material, such as porcelain or ceramic or when faced with such material;

The provision of such a bracket which is self-ligating and which saves time for both the patient and for the orthodontist, in that it reduces the time necessary for handling and adjusting the wire within the appliance especially when the brackets are positioned on the lingual side of the teeth; and The provision of such a bracket which may be readily bonded to a desired surface of the tooth, which is compact in size, which is comfortable to wear, and which does not adversely affect the patient's appearance above and beyond the requirement of having to wear an arch wire.

Other objects and features of this invention will be in part apparent and in part pointed out hereinafter.

Briefly stated, this invention relates to an orthodontic bracket having a body, with the body having a face adapted to be secured to the face of a tooth and a slot for receiving an arch wire. The bracket has means for resiliently biasing the wire into the slot and for holding the wire in the slot. This biasing and holding means comprises a wire engaging platen movable toward and away from the slot and biasing means for positively biasing the wire engagement member toward the slot, said wire engaging member being substantially axially movable toward and away from the slot between a retracted position in which the wire may be readily inserted in and removed from said bracket, and a retaining position in which said platen positively engages the arch wire.

BRIEF DESCRIPTION OF THE DRAWINGS

Corresponding reference characters indicate corresponding parts throughout the several views of the drawings.

DESCRIPTION OF A PREFERRED EMBODIMENT

Figure 1:
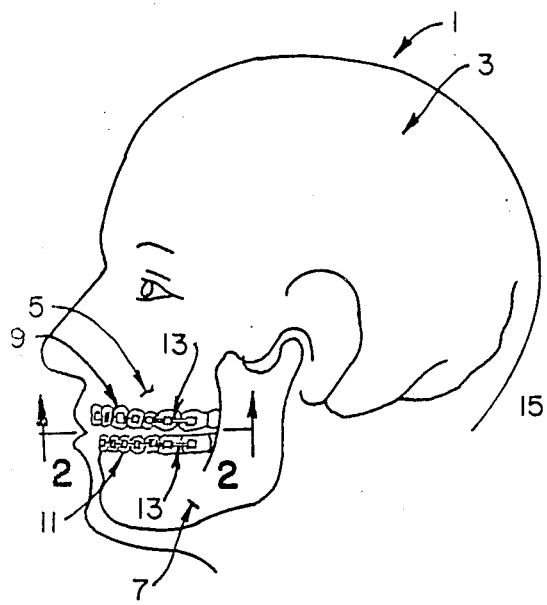
FIG. 1 is a side elevational view of a patient's head, illustrating the key skeletal and dental anatomical features of the patient's head.

Referring now to the drawings, and more particularly to FIG. 1, a patient's head is generally indicated at 1. The head, of course, includes a skull 3. The skeleton of the face includes the maxilla 5 in which the teeth of the upper jaw are embedded and the mandible 7 in which the teeth of the lower jaw are embedded. The teeth of the upper jaw are referred to as the upper arch and are generally indicated by reference character 9, while the teeth of the lower jaw are generally referred to as the lower arch and are indicated generally by reference character 11.

Figure 2:
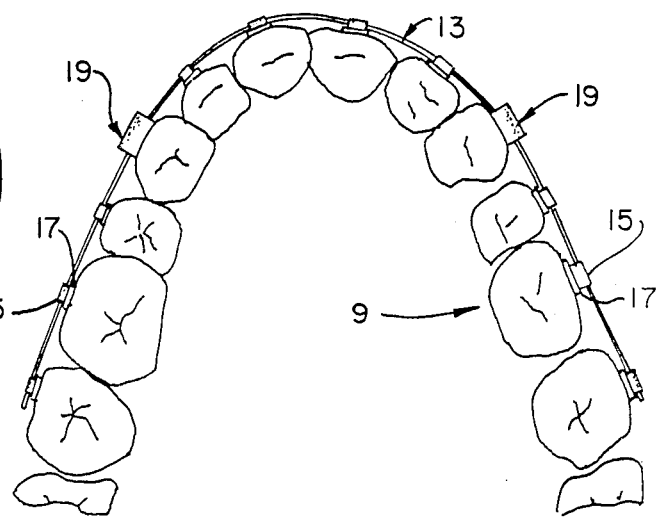
FIG. 2 is a view, taken along line 2—2 of FIG. 1, illustrating, in an enlarged scale, the teeth of the patient's upper arch with an arch wire carried by tubes which in turn are secured to pads bonded to the outer face of the teeth of the upper arch, with certain of the teeth of the upper arch having brackets of the present invention bonded thereto.

As illustrated in FIG. 1, the teeth of the upper arch 9 and the teeth of the lower arch 11 may each have a respective outer (buccal) arch wire 13 affixed thereto for carrying out a variety of desired orthodontic treatments as are well known to those skilled in the art. Generally, arch wire 13 is carried by a plurality of tubes or brackets 15, as best shown in FIG. 2, each of which is carried by a pad 17 bonded to the outer face of a respective tooth. In the conventional and well known manner, these arch wires may be utilized in conjunction with various springs and elastomeric orthodontic appliances to apply a variety of desired forces which, as determined by the treating orthodontist, may be required to orthodontically treat the patient's teeth. In accordance with this invention a lingual archwire (not shown) may be installed on the lingual (inside) faces of the teeth shown in FIG. 2. A detailed description of the various orthodontic force application applying apparatus and techniques is not herein required because these are well known to those skilled in the art.

Figure 3:
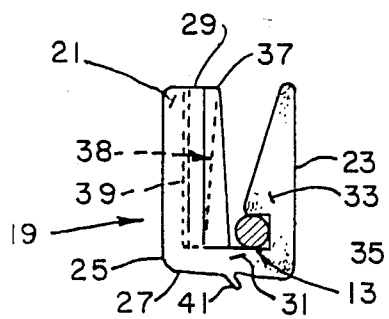
FIG. 3 is a view, on a substantially enlarged scale, of an orthodontic bracket of the present invention, with the lower or bottom end of the bracket (as shown in FIG. 3) being disposed toward the occlusal end of the tooth, and with the platen of the bracket retracted so as to permit the ready insertion and removal of the arch wire from the bracket.
Figure 5:
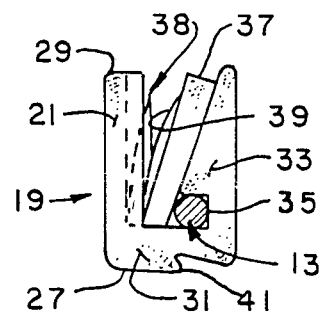
FIG. 5 is a view similar to FIG. 3, in which the wire engaging platen of the bracket of the present invention is in engagement with the arch wire thereby to positively hold the arch wire relative to the bracket.

In accordance with this invention, a bracket, as generally indicated at 19, is secured to a face, either the outer (buccal) face of a selected tooth as shown in FIG. 2 or the lingual face of the tooth (not shown) for receiving and holding arch wire 13 so as to transmit an orthodontic corrective force to or from the tooth on which bracket 19 is applied. As shown in FIG. 2, bracket 19 comprises a body 21 having inner side 23 adapted to be secured (bonded) to a face of a tooth and outer side 25. The body has an occlusal end 27 and a gingival end 29. The body 21 consists of a base 31 and an anvil 33 spaced from the base. A slot 35 is provided in the anvil for receiving arch wire 13. The bracket 19 further has a platen 37 which is movable relative to base 31 toward and away from anvil 33 from a retracted position, such as shown in FIG. 3, in which the wire 13 may be readily inserted into and removed from slot 35, and a wire gripping position, as shown in FIG. 5, in which the platen engages the wire and forces the wire into the slot whereby the wire is positively held with respect to the bracket thereby enabling desired orthodontic corrective forces to be transmitted between the wire and the tooth to which bracket 19 is attached.

Figure 4:
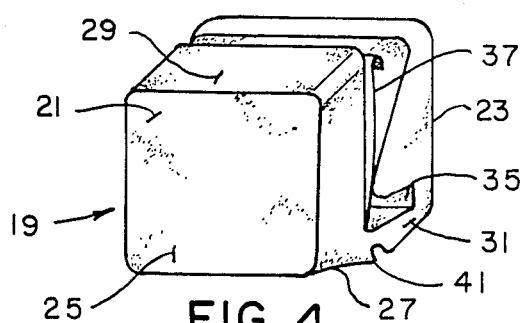
FIG. 4 is a side perspective view of the bracket illustrated in FIG. 3.

Further, in accordance with this invention, means, as indicated at 38, resiliently biases platen 37 toward its wire gripping position relative to base 31. As shown in FIGS. 3–5, this wire biasing means is constituted by a compression coil spring 39 interposed between the base and the platen. Spring 39 is initially compressed such that when the wire is inserted into the bracket, in register with slot 35, further compression of the spring results such that the spring exerts a constant pressure force on the wire thereby to retain it in the bracket and to increase its orthodontic corrective effect.

It will be understood that arch wire 13 typically constitutes the active component of certain types of orthodontic appliances utilizes to move or position teeth. Generally, previous orthodontic brackets, such as shown in U.S. Pat. No. 3,835,539, have a slot which receives an arch wire. The bracket typically is available with slots of two different dimensions, a heavy wire oriented slot having a width of 0.022 inch and a length of 0.028 inch, and a lightwire slot having a width of 0.018 inch and a length of 0.022 inch. With prior art brackets, to change from a lightwire to a heavy wire or vice-versa required that a new bracket with a properly corresponding slot dimension be adhered to the teeth.

It will be understood that the bracket 19 of the present invention, with the movable platen 37, permits a treating orthodontist to use either a light archwire or a heavy archwire without the necessity of having to change brackets.

It will also be understood that within combination with arch wire 13, a treating orthodontist may use springs or elastomer bands to apply other corrective orthodontic forces to the teeth. To aid in this matter, elastomeric spring attachment hooks 41 may be provided on bracket body 21.

Those skilled in the art will also recognize that because spring 39 applies a continuous retaining force with arch wire 13, because the bracket 19 may secure the archwire at any position therealong, and because the bracket 19 may accommodate wires of various diameters, bracket 19 of the present invention is self-ligating (i.e., it automatically secures the archwire to the bracket). More specifically, the treating orthodontist may move wire 13 within the bracket and upon cessation of movement of the wire, the platen will automatically and substantially instantaneously grip the wire thereby to maintain a desired force level and direction on the orthodontic wire without the necessity of tying or ligating the wire with respect to the brackets without the need of ligating pliers or other instruments.

Further, it will be noted that the vertical space between base 31 and anvil 33 of bracket body 21 allows the use auxiliary springs or elastomeric bands (not shown) so as to permit the treating orthodontist to apply uprighting or torque control to selected teeth.

Further in accordance with this invention, it will be understood that bracket body 21 may be made of any number of different materials, including metal. However, the bracket body may also be a cosmetic bracket of the same color as the teeth, a suitable porcelain or ceramic material. In the alternative, the bracket may be faced or coated with such a cosmetic material.

Figure 6:
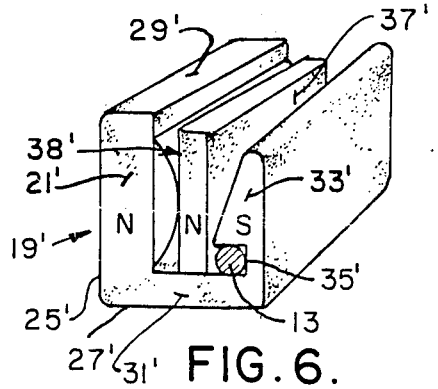
FIG. 6 is a perspective view of another embodiment of the bracket of the present invention in which magnetic forces are utilized so as to resiliently bias the wire engaging platen into engagement with the arch wire and for holding the wire engaging platen in engagement with the arch wire.

Referring now to FIG. 6, a different embodiment of the bracket of the instant invention is indicated in its entirety by reference character 19'. It will be understood that corresponding parts of this other bracket 19' with the primed reference characters in FIG. 6 indicate parts having a corresponding construction and function as similar parts in bracket 19, as illustrated in FIGS. 3–5. It will be understood that, except for the biasing means 38', bracket 19' is essentially identical in size, construction, and function as bracket 19 described above. However, in bracket 19', biasing means 38' comprises a magnet, the construction of which will be hereinafter described, which magnetically biases platen 37' into firm engagement with arch wire 13 received in slot 35' in base 31'. More specifically, this biasing means comprises a magnetic pole, e.g., a north pole, located in base 31. Another pole of similar magnetic orientation, e.g., a north pole, is located in platen 37 ', such that the similar poles of the magnetic biasing means 38' repel one another and thus force plate 37' into firm engagement with arch wire 13 received in slot 35'. It will further be understood that, optionally, anvil 33, may carry a magnet having a pole of opposite sense, e.g., a south pole, so as to positively attract the platen 37' into engagement with the arch wire, thus creating additional force.

In use, the inner faces 23 of brackets 19 (or 19',) are adhered (bonded) to the faces of the teeth of a selected arch, for example, the upper arch 9, as shown in FIGS. 1 and 2. As heretofore noted, the archwire may either be on the buccal or lingual side of the arch. These brackets are utilized in place of the adhesive pads 17 heretofore used in conjunction with arch wire tubes 15, or in place of prior art brackets, such as shown in U.S. Pat. No. 3,835,539. The brackets are oriented on the outer surface of the teeth with the open end of the space between base 31 and anvil 33 oriented gingivally (toward the gums). With the brackets so adhered to the faces of the teeth, arch wire 13 is inserted into the brackets by fitting the wires into the opening between the anvil and the base and forcing the arch wire downwardly thereby forceably moving platen 37 toward its retracted position and applying additional compressive forces to spring 39. As wire 13 moves into register with slot 35, a biasing force of spring 39 acts against the wire via the lower margins of platen 37, thus wedgingly forcing the arch wires into slot 35 thereby to hold the arch wire with respect to the bracket and to permit desired orthodontic correction forces to be applied to the teeth via the brackets. As heretofore explained, suitable elastic springs (not shown) may be attached at desired locations on bracket body 21 by means of elastic attachment hooks 41 provided on the bracket bodies.

In view of the above, it will be seen that the other objects of this invention are achieved and other advantageous results obtained.

As various changes could be made in the above constructions without departing from the scope of the invention, it is intended that all matter contained in the above description or shown in the accompanying drawing shall be interpreted as illustrative and not in a limiting sense. For example the conventional bracket may be designed to accommodate either a conventional edgewise bracket, or as a straight wire applied bracket. Other modifications will occur to those skilled in the art.

What is claimed is:

1. An orthodontic bracket having a body, said body having a first portion disposed proximate a tooth, said first portion having a face adapted to be secured to said tooth and a slot for receiving an orthodontic arch wire, said body having a second portion spaced from said first portion and defining an archwire receiving opening therebetween, said second portion having means for wedgingly, resiliently biasing the arch wire into said slot and for self-ligation holding of said arch wire within said slot, said resilient holding means comprising a wire engaging member movable relative to said second portion toward and away from said slot such that upon introducing a wire into said opening said wire is resiliently biased by said wire engaging member into said slot and is resiliently held by said wire engaging member with respect to said bracket at any position along said wire so as to apply and maintain a relative constant level of orthodontic corrective force to even upon movement of said tooth.

2. An orthodontic bracket as set forth in claim 1 wherein said biasing means comprises a compression spring interposed between said second portion of said bracket body and said wire engaging member with said spring being substantially axially oriented between said second body portion and said wire engaging member.

3. An orthodontic bracket as set forth in claim 2 wherein said second portion of said body has a spring compartment therewithin, and wherein said wire engaging member comprises a platen movable toward and away from said slot, said spring being received in said spring compartment and being interposed between said second body portion and said platen with said spring biasing said platen and said wire toward said slot.

4. An orthodontic bracket as set forth in claim 1 wherein said biasing means comprises means for magnetically biasing said wire engaging element into engagement with said wire thereby to hold said wire within said slot.

* * * * *